United States Patent [19]

Horodysky et al.

[11] Patent Number: 5,126,397
[45] Date of Patent: Jun. 30, 1992

[54] QUATERNARY AMMONIUM SALT DERIVED THIADIAZOLES AS MULTIFUNCTIONAL ANTIOXIDANT AND ANTIWEAR ADDITIVES

[75] Inventors: Andrew G. Horodysky, Cherry Hill, N.J.; Shih-Ying Hsu, Morrisville, Pa.

[73] Assignee: Mobil Oil Corporation, Fairfax, Va.

[21] Appl. No.: 668,664

[22] Filed: Mar. 13, 1991

[51] Int. Cl.$^5$ .......................................... C10M 135/36
[52] U.S. Cl. .................................. 252/34; 252/47.5; 548/141; 548/142
[58] Field of Search ............... 252/47.5, 34; 548/141, 548/142

[56] References Cited

U.S. PATENT DOCUMENTS

| | | | |
|---|---|---|---|
| 2,760,933 | 8/1956 | Fields | 252/47.5 |
| 3,914,241 | 10/1975 | Elliot | 548/142 |
| 3,940,408 | 2/1976 | Waldbillig | 548/141 |
| 4,136,043 | 1/1979 | Davis | 252/47.5 |
| 4,140,643 | 2/1979 | Davis | 252/47.5 |
| 4,246,126 | 1/1981 | Arakelian | 548/142 |
| 4,301,019 | 11/1981 | Horodysky | 548/141 |
| 4,315,889 | 2/1982 | McChesney | 252/34 |
| 4,410,703 | 10/1983 | Okorodudu | 548/142 |
| 4,584,114 | 4/1986 | Gemmill et al. | 252/47.5 |
| 4,661,273 | 4/1987 | Frangatos et al. | 252/47 |
| 4,678,592 | 7/1987 | Toukan | 252/25 |
| 4,908,144 | 3/1990 | Davis | 548/142 |
| 5,055,584 | 10/1991 | Karol | 548/142 |

FOREIGN PATENT DOCUMENTS 750983  6/1956  United Kingdom.

Primary Examiner—Prince Willis, Jr.
Assistant Examiner—Steinberg
Attorney, Agent, or Firm—Alexander J. McKillop; Charles J. Speciale; Howard M. Flournoy

[57] ABSTRACT

Quaternary ammonium salt derived thiadiazoles provide multifunctional antioxidant/antiwear characteristics to lubricants when incorporated therein.

11 Claims, No Drawings

QUATERNARY AMMONIUM SALT DERIVED THIADIAZOLES AS MULTIFUNCTIONAL ANTIOXIDANT AND ANTIWEAR ADDITIVES

BACKGROUND OF THE INVENTION

1. Field of the Invention

This application is directed to quaternary ammonium salt reaction products derived from heterocyclics such as thiadiazoles as multifunctional antioxidant/antiwear additives for lubricants and fuels and to compositions containing same.

2. Description of Related Art

The use of thiadiazole derivatives, such as 2,5-dimercapto-1,2,4-thiadiazole, for their antioxidant, anticorrosion and metal passivating properties when incorporated into oleaginous compositions is well known as disclosed in U.S. Pat. Nos. 4,661,273, 4,678,592 and 4,584,114. U.S. Pat. No. 4,410,703 discloses the use of thiadiazoles substituted with other moieties such as the organophosphorous moiety.

The use of alkenyl succinic acid-esters has been reported as rust inhibitors and dispersants for a variety of lubricating oils and greases.

However, organic ammonium salt antioxidants have received little or no attention in the past as lubricant additives. While developing new antioxidants for mineral oil base stock and synthetic stock based lubricants, we discovered that organic ammonium salts could display remarkable antioxidant and antiwear properties when derivatized with certain synergistic hetercyclic species. The key design of this class of unique antioxidant appears to be the combination of an antioxidant moiety and an organic cation. Various types of antioxidant and organic cations can be used effectively. The resulting products are generally soluble in synthetic lubricants; including synthetic hydrocarbon esters and the like. Many are also soluble in less polar mineral base stocks containing high percentages of paraffinic or paraffinic-like components. Solubility in mixed base stocks formulated with mixtures of synthetic and mineral oil blending components is good.

SUMMARY OF THE INVENTION

This invention more particularly provides quaternary ammonium salts derived from heterocycles having one or two mercaptan functionalities, e.g., thiadiazoles, as multifunctional lubricant and fuel additives and fuel and lubricant compositions comprised thereof.

The invention accordingly provides compounds illustrated by the selected examples represented by the following generalized formulas:

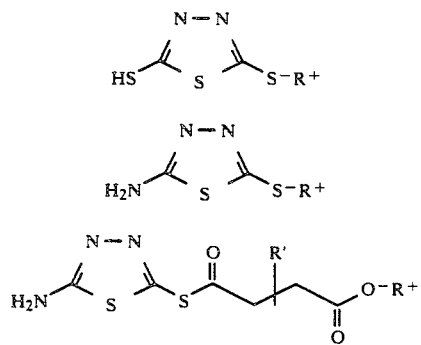

+ Others

Where $R^+$ = tetrasubstituted ammonium ion in which each substituted group attached to nitrogen can be the same or different; and can be hydrocarbyl, preferably $C_1$ to about $C_{18}$, or aryl and can optionally contain sulfur, nitrogen and/or oxygen; $R' = C_1$ to about $C_{60}$ hydrocarbyl, such as alkyl or alkenyl or a polyhydrocarbyl such as polyisobutenyl, or polypropenyl.

Organic ammonium salts disclosed in this patent information are a new class of antioxidants and show good antioxidancy performance. To the best of our knowledge, these classes of antioxidants have not been synthesized or manufactured elsewhere. Their synthesis and application as antioxidants are novel, as is their use as multifunctional antioxidant, antiwear, corrosion inhibiting and metal passivating additives. They are also expected to impart antirust, thermal stabilizing, extreme pressure, antifatigue, friction reducing, detergency, and emulsifying or demulsifying properties to both lubricants and fuels. Included are oxygenated fuels, hydrocarbon fuels and next-generation "clean fuels".

It is, therefore, an object of this invention to provide improved lubricant and fuel compositions, novel multifunctional lubricant and fuel additives and the novel use of the described additives in such compositions.

DESCRIPTION OF PREFERRED EMBODIMENTS

The organic ammonium salt antioxidants based for example, on 2,5-dimercapto-1,3,4-thiadiazole (DMTD) and/or 6-amino-1,3,4-thiadiazole-2-thiol can be generally prepared as shown in equations 1 and 2. These two heterocycles are used for illustration purpose only. Any heterocyclic compound with one or two mercaptan functionality (i.e. —SH) derivatized the same way falls within the scope of the claims of this invention. Sodium hydroxide can be used as the base (Equation 1); other organic bases can also be used, such as triethylamine, pyridium, etc, or similar amine or nitrogen-containing bases. However, preferred are the alkali or alkaline-earth metal hydroxides. Especially preferred are sodium and potassium hydroxide.

The resulting products are one-side capped and are generally soluble in ester-based lubricants and other synthetic lubricants to give good antioxidancy.

Although alkyl succinic anhydride is illustrated, any similar aliphatic or aromatic dibasic anhydride can be used to advantage.

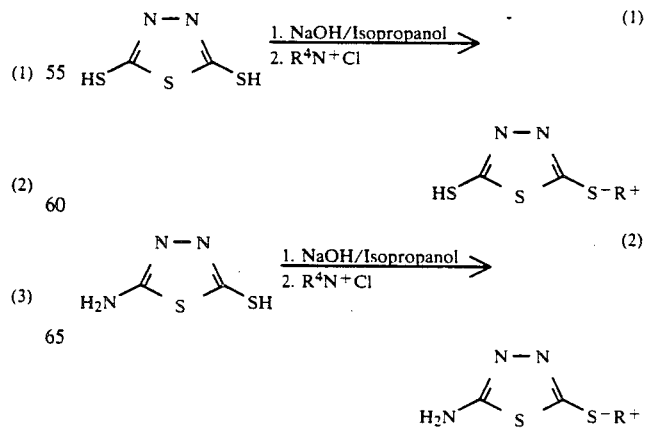

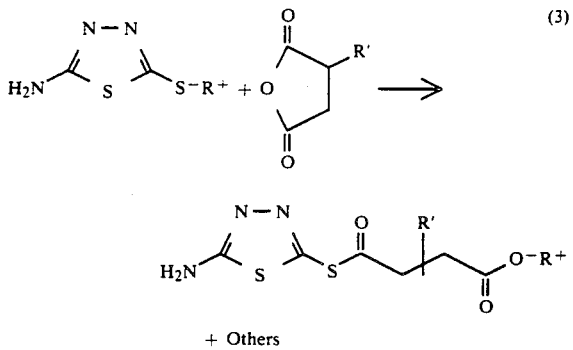

+ Others

Where $R^+$ = the tetrasubstituted ammonium ion in which each substituted group attached to nitrogen can be the same or different; and can be hydrocarbyl, preferably $C_1$-$C_{18}$, or aryl and can optionally contain sulfur, nitrogen and/or oxygen; $R' = C_1$-$C_{18}$ hydrocarbyl, selected preferably from alkyl or alkenyl or is polyhydrocarbyl such as polyisobutenyl, or polypropenyl.

Suitable thiadiazoles include any appropriate mercapto-thiadiazole, however, preferred is 2,5-dimercapto-1,3,4-thiadiazole. Some other suitable examples include but are not limited to 3,4-dimercapto-1,2,5-thiadiazole, 3,5-dimercapto-1,2,4-thiadiazole, 4,5-dimercapto-1,2,5-thiadiazole, 4,5-dimercaptobenzo-1,2,3-thiadiazole, 4,7-dimercaptobenzo 1,2,3-thiadiazole, 4,6-dimercaptobenzo 1,2,3-thiadiazole, 5,6-dimercaptobenzo- 1,2,3-thiadiazole, 5,7-dimercaptobenzo 1,2,3-thiadiazole, 6,7-dimercaptobenzo 1,2,3-thiadiazole, 4,5-dimercaptobenzo-2,1,3-thiadiazole, 4,6-dimercaptobenzo 2,1,3-thiadiazole, 5,6-dimercaptobenzo 2,1,3-thiadiazole, 5,7-dimercaptobenzo-2,1,3-thiadiazole, 6,7-dimercaptobenzo 2,1,3-thiadiazole and 5-amino-1-3-4-thiadiazole-2-thiol.

Suitable hydrocarbyl anhydrides include alkyl or alkenyl succcinic anhydrides or any similar aliphatic or aromatic dibasic anhydrides or their corresponding acids. Examples include but are not limited to phthatic acids or anhydrides, hydrocarbyl substituted phthatic acids or anhydrides, pyromellitic anhydride derivatives, dimer acids such as dimerized oleic acid and the like. They generally contain from about 4 to about 100 carbon atoms.

Conditions for the above reactions may vary widely depending upon specific reactants, the presence or absence of a solvent and the like. Any suitable set of reaction conditions known to the art may be used. Hydrocarbon solvents such as toluene or mixed xylenes are frequently used. Generally stoichiometric or equimolar ratios of reactants are used. However, more than molar or less than molar amounts may also be used. Temperatures may vary from ambient to about 150° C. and the pressure is generally ambient or autogenous and the reaction times may vary from 1 to about 8 hours or more. In any event, reaction conditions are not viewed as critical.

The additives embodied herein are utilized in lubricating oil or grease compositions in an amount which imparts significant antioxidant and antiwear characteristics to the oil or grease as well as reducing the friction of engines operating with the oil in its crankcase. Concentrations of about 0.001 to about 10 wt. % based on the total weight of the composition can be used. Preferably, the concentration is from 0.1 to about 3 wt. %.

It is expected that these materials would also be suitable for use in liquid hydrocarbyl, i.e. liquid hydrocarbon combustion fuels such as gasoline, or alcoholic or mixed hydrocarbyl/alcoholic or oxygenated fuel composition as well as distillate fuels, fuel oils, jet fuels and next-generation "clean fuels. They are utilized in fuels in amounts of from about 25 to 500 pounds of additive per thousand barrels of fuel and preferably from about 50 to about 250 pounds per 1000 barrels of fuel.

The additives have the ability to improve the above noted characteristics of various oleagenous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100.F and preferably, from about 50 to about 250 SSU at 210° F. These oils may have viscosity indexes ranging to about 100 or higher. Viscosity indexes ranging from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers. Ester-based lubricants, in general, are highly suitable.

It is to be understood, however, that the compositions contemplated herein can also contain other materials. For example, corrosion inhibitors, extreme pressure agents, low temperature properties modifiers and the like can be used as exemplified respectively by metallic phenates and/or sulfonates, polymeric succinimides, non-metallic or metallic phosphorodithioates, aryl amines, hindered phenols, sulfurized olefins, esters and/or amides or imides and the like. These materials do not detract from the value of the compositions of this invention, rather the materials serve to impart their customary properties to the particular compositions in which they are incorporated.

The following examples are merely illustrative and not meant to be limitations.

EXAMPLE 1

To a solution of 2,5-dimercapto-1,3,4-thiadiazole (30 g, 0.2 mol) in methanol (200 ml) was added sodium hydroxide (8 g, 0.2 mol) at ambient temperature. The solution was stirred for 30 min. and Aliquat 336 (tricaprylylmethylammonium chloride 81 g, 0.2 mol) was slowly added. Sodium chloride precipitated out during the addition. When the addition was complete, stirring was continued at ambient temperature for one hour. The mixture was filtered and the solvent was evaporated to afford the product as a greenish oil (102 g, 98%).

EXAMPLE 2

To a solution of 2-amino-5-mercapto-1,3,4-thiadiazole (20 g, 0.15 mol) in isopropanol (100 ml) was added potassium hydroxide (8.4 g, 0.15 mol) at ambient temperature. (Sodium hydroxide can also be used.) The solution was stirred for 30 min and Aliquat 336 (61 g, 0.15 mol, tricaprylmethylammonium chloride) was slowly added. Potassium chloride precipitated out during the addition. When the addition was complete, stirring was continued at ambient temperature for one hour. The mixture was filtered and the solvent was evaporated to give a dark brownish oil which was immediately reacted with 2-dodecen-1-yl succinic anhydride (40 g, 0.15 mol) at 70-80.C to afford the final product as a brownish oil (110 g, 96%).

EVALUATION OF PRODUCTS

The organic ammonium salt antioxidants thus obtained were blended into pentaerythritol derived ester lubricants and evaluated for antioxidant performance by the Catalytic Oxidation Test at 425° F. for 24 hours (Table 1). A comparison of the oxidation-inhibiting characteristics of the novel products in accordance with the invention with commercially available hindered phenolic antioxidants in the same base stocks was conducted side by side; results are included in Table 1.

CATALYTIC OXIDATION TEST

Basically, in the catalytic oxidation test, the lubricant is subjected to a stream of air which is bubbled through the lubricant at the rate of five liters per hour at elevated temperatures for a specified time (Table 1, 425° F. for 24 hours). Present in the composition are samples of metals commonly used in engine construction, namely, iron, copper, aluminum, and lead. For further details, see U.S. Pat. No. 3,682,980, incorporated herein by reference.

TABLE 1

| ITEM | Catalytic Oxidation Test (425° F., 24 hr) | | |
|---|---|---|---|
| | ADDITIVE CONCENTRATION (WT %) | CHANGE IN ACID NUMBER Δ TAN | % CHANGE IN VISCOSITY Δ KV, % |
| Base oil (Pentaerythritol derived ester lubricant) | None | 8 | 684 |
| Commercial Phenolic Antioxidant (Ethyl Corp., Ethyl 702) in above oil | 1.0 | 5.0 | 96.9 |
| Example 1 in above oil | 1.0 | 2.4 | 32.2 |
| Example 2 in above oil | 1.0 | 4.3 | 60.9 |

Clearly the use of these quaternary ammonium salt derived thiadiazole reaction products and their subsequent hydrocarbyl anhydride derivatives provide exceptional antiwear and antioxidant activity with corrosion inhibiting and metal passivating properties. The compositions of this invention also provide antiwear benefits not provided by traditional antioxidants.

The organic quaternary ammonium salt antioxidants are a novel and unique class of compounds which exhibit very good performance in ester-based lubricants under severe service conditions as exemplified by above test data. These properties can enhance the thermal and oxidative stability of premium quality automotive and industrial lubricants, greases and fuels to extend their service life. These compounds can be easily manufactured with known additive technologies.

What is claimed is:

1. An improved lubricant composition comprising a major proportion of a multifunctional antiwear, antioxidant, corrosion inhibiting additive product of reaction obtained by reacting (1) a thiadiazole derivative having one amino functionality with a quaternary ammonium salt and (2) the product thereof with an organic dibasic anhydride in substantially molar amounts at temperatures varying from ambient to about 150° C. under ambient or autogenous pressures for a time sufficient to obtain the desired additive product.

2. The composition of claim 1 wherein the product of reaction (1) has the following structural formula:

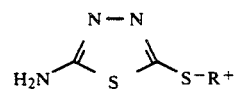

and wherein R+ = tetrasubstituted ammonium ion and wherein each substituted group is the same or different and is $C_1$ to about $C_{18}$ hydrocarbyl or $C_1$ to about $C_{18}$ hydrocarbyl optionally containing sulfur, nitrogen acid-/or oxygen.

3. The composition of claim 1 wherein said product comprises at least one reaction product or products with the following structural formula:

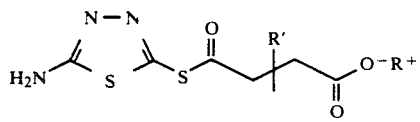

Where $R^+$ = hydrocarbyl tetrasubstituted ammonium ion wherein each substituted group is a $C_1$ to about $C_{18}$ hydrocarbyl group or $C_1$ to about a $C_{18}$ hydrocarbyl group optionally containing sulfur, nitrogen and/or oxygen; $R' = C_1$ to about $C_{18}$ hydrocarbyl or polyhydrocarbyl where hydrocarbyl is selected from alkyl or alkenyl and each substituted group is the same or different.

4. The composition of claim 1 wherein the thiadiazole is 2-amino-5-mercapto-1,3,4-thiadiazole and the quaternary ammonium salt is tricaprylmethylammonium chloride.

5. The composition of claim 1 wherein the organic dibasic anhydride is 2-dodecen-1-yl succinic anhydride.

6. The composition of claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1), (2) or (3).

7. The composition of claim 6 wherein the lubricant contains from about 0.001 to about 10 wt % based on the total weight of the composition of the additive product of reaction.

8. The composition of claim 6 wherein the lubricant is a synthetic oil.

9. The composition of claim 8 wherein the lubricant is a pentaerythritol derived ester oil.

10. A method of preparing an improved lubricant composition comprising adding to said lubricant a minor multifunctional antioxidant, antiwear, corrosion inhibiting or metal passivating amount of an additive product of reaction as described in claim 1.

11. A method of claim 10 wherein said composition is a lubricant composition and said minor amount is from about 0.001 to about 10 wt % of said additive product of reaction, based on the total weight of the composition.

* * * * *